US010426607B2

(12) United States Patent
Gregg et al.

(10) Patent No.: US 10,426,607 B2
(45) Date of Patent: Oct. 1, 2019

(54) APPARATUS FOR REPLACING A NATIVE HEART VALVE AND METHOD OF MAKING THE SAME

(71) Applicant: BOSTON SCIENTIFIC SCIMED, INC., Maple Grove, MN (US)

(72) Inventors: Peter W. Gregg, Santa Cruz, CA (US); Jianhua Yang, Saratoga, CA (US); Jarad Waisblatt, San Jose, CA (US); Benjamin T. Sutton, Scotts Valley, CA (US); Ali Salahieh, Saratoga, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 463 days.

(21) Appl. No.: 14/820,171

(22) Filed: Aug. 6, 2015

(65) Prior Publication Data

US 2015/0335423 A1    Nov. 26, 2015

Related U.S. Application Data

(63) Continuation of application No. 13/911,515, filed on Jun. 6, 2013, now abandoned.
(Continued)

(51) Int. Cl.
*A61F 2/24* (2006.01)
*A61F 2/90* (2013.01)

(52) U.S. Cl.
CPC ........... *A61F 2/2412* (2013.01); *A61F 2/243* (2013.01); *A61F 2/2418* (2013.01);
(Continued)

(58) Field of Classification Search
CPC .... A61F 2/2418; A61F 2/2415; A61F 2/2412; A61F 2/2409; A61F 2/2403; A61F 2/24;
(Continued)

(56) References Cited

U.S. PATENT DOCUMENTS 5,061,275 A    10/1991   Wallstén et al.
6,221,100 B1    4/2001   Strecker
(Continued)

FOREIGN PATENT DOCUMENTS

DE    102010048368 A1    4/2012
EP         1872743 A1    1/2008
(Continued)

OTHER PUBLICATIONS

Wei, Guangxu, "High Cycle Compressive Fatigue of Unidirectional Glass/Plyester Performed at High Frequency, a Thesis submitted in partial fulfillment of the requirements for the degree of Master of Science in Chemical Engineering," Montana State University, Bozeman, Montana, Jul. 1995.
(Continued)

*Primary Examiner* — Darwin P Erezo
*Assistant Examiner* — Katherine H Schwiker
(74) *Attorney, Agent, or Firm* — Seager, Tufte & Wickhem LLP (57) ABSTRACT

An apparatus for replacement a native heart valve is herein provided. The apparatus includes a replacement heart valve, an expandable anchor, and a plurality of rivets. The expandable anchor comprises a woven braid structure that surrounds at least a portion of the replacement heart valve and has a plurality of braid intersections. At least some of the braid intersections have rivets extending therethrough.

17 Claims, 12 Drawing Sheets

Related U.S. Application Data (60) Provisional application No. 61/656,746, filed on Jun. 7, 2012.

(52) U.S. Cl.
CPC .............. *A61F 2/2427* (2013.01); *A61F 2/90* (2013.01); *A61F 2220/0041* (2013.01)

(58) Field of Classification Search
CPC .... A61F 2/24; A61F 2/90; A61F 2/915; A61F 2220/0016; A61F 2220/0075; A61F 2230/0054; A61F 2/2406; A61F 2/91; A61B 2002/91508; A61B 2002/91516; A61B 2002/91525; A61B 2002/91533; A61B 2002/91541; A61B 2002/9155; A61B 2002/91558; A61B 2002/91566; A61B 2002/91575; A61B 2002/91583; A61B 2002/91591
See application file for complete search history.

(56) References Cited

U.S. PATENT DOCUMENTS

| | | |
|---|---|---|
| 7,135,039 B2 | 11/2006 | De Scheerder et al. |
| 7,213,495 B2 | 5/2007 | McCullagh et al. |
| 2003/0088307 A1 | 5/2003 | Shulze et al. |
| 2003/0144728 A1 | 7/2003 | Scheuermann et al. |
| 2004/0049266 A1* | 3/2004 | Anduiza ............... A61F 2/2418 623/2.11 |
| 2005/0137702 A1 | 6/2005 | Haug et al. |
| 2005/0143809 A1 | 6/2005 | Salahieh et al. |
| 2005/0228480 A1 | 10/2005 | Douglas et al. |
| 2006/0184238 A1 | 8/2006 | Kaufmann et al. |
| 2007/0239273 A1 | 10/2007 | Allen |
| 2008/0004696 A1* | 1/2008 | Vesely ................... A61F 2/2418 623/2.1 |
| 2008/0195199 A1* | 8/2008 | Kheradvar ............ A61F 2/2418 623/2.11 |
| 2009/0054972 A1* | 2/2009 | Norton ....................... A61F 2/90 623/1.53 |
| 2010/0280587 A1 | 11/2010 | Ortiz et al. |
| 2010/0318171 A1 | 12/2010 | Porter et al. |
| 2011/0054589 A1 | 3/2011 | Bashiri et al. |
| 2011/0230956 A1 | 9/2011 | White |
| 2011/0251670 A1* | 10/2011 | Kheradvar .............. A61F 2/915 623/1.15 |
| 2013/0046373 A1* | 2/2013 | Cartledge ................. A61F 2/95 623/1.11 |

FOREIGN PATENT DOCUMENTS

| | | |
|---|---|---|
| WO | 2005062980 A2 | 7/2005 |
| WO | 2006071906 A1 | 7/2006 |
| WO | 2010011699 A2 | 1/2010 |

OTHER PUBLICATIONS

All non-patent literature documents and foreign patent documents have been previously uploaded in parent U.S. Appl. No. 13/911,515.

* cited by examiner

APPARATUS FOR REPLACING A NATIVE HEART VALVE AND METHOD OF MAKING THE SAME

CROSS-REFERENCE TO RELATED APPLICATIONS

This application is a continuation of U.S. application Ser. No. 13/911,515, filed Jun. 6, 2013, which claims the benefit of and priority to U.S. Provisional Application No. 61/656,746, filed Jun. 7, 2012, the entire contents of which are herein incorporated by reference.

STATEMENT REGARDING FEDERALLY SPONSORED RESEARCH

Not Applicable

BACKGROUND OF THE INVENTION

Various types of replacement heart valve stents and devices are known in the art. In particular, self-expanding medical devices are widely used in percutaneous implantation. Certain types of these devices suffer from a number of drawbacks, however. In particular, when used to replace heart valves, these devices undergo cyclical loading due to the opening and closing of the valve. These cyclical loads can translate into fatigue, which is undesirable because it can cause valve failure having catastrophic implications for the patient. Consequently, there remains a need for a replacement heart valve and anchor with increased fatigue resistance.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. .sctn.1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

BRIEF SUMMARY OF THE INVENTION

In some embodiments, an apparatus for replacing a native heart valve comprises an expandable anchor and a replacement heart valve attached to the expandable anchor. In some embodiments, the apparatus further comprises a plurality of rivets. In some embodiments, the expandable anchor comprises a woven braid structure surrounding at least a portion of the replacement heart valve, the woven braid structure having a plurality of braid intersections. In some embodiments, each braid intersection has a first wire segment and a second wire segment overlapping the first wire segment. In some embodiments, one of the rivets extends through the first wire segment and the second wire segment at the braid intersection, the first wire segment is hingeable with respect to the second wire segment.

DETAILED DESCRIPTION OF THE INVENTION

While this invention may be embodied in many different forms, there are described in detail herein specific embodiments. This description is an exemplification of the principles of the invention and is not intended to limit it to the particular embodiments illustrated.

For the purposes of this disclosure, like reference numerals in the figures shall refer to like features unless otherwise indicated.

Figure 1:
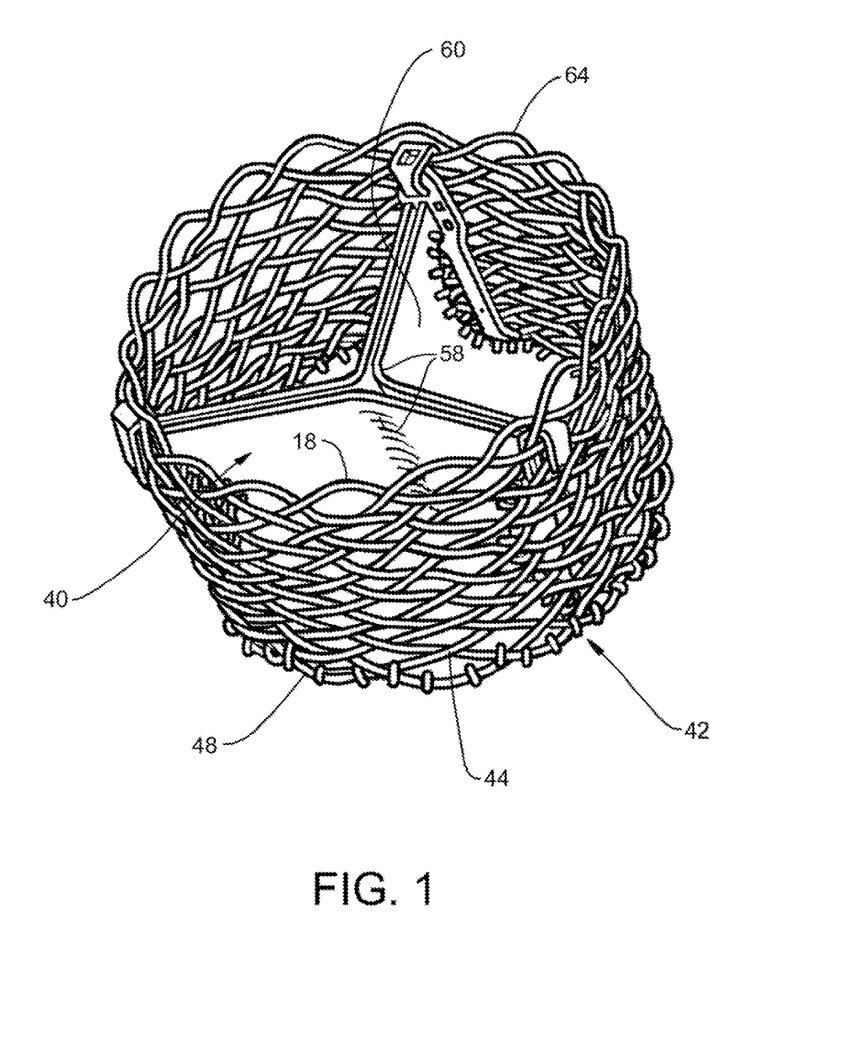
FIG. 1 is a perspective view of a replacement heart valve and anchor.

In some embodiments, an apparatus for replacing a native heart valve comprises a replacement heart valve 40 and an anchor 42. In some embodiments, the anchor 42 comprises a woven braid structure, for example as shown in FIG. 1. The woven braid structure comprises a plurality of braid intersections 44.

Figure 2A:
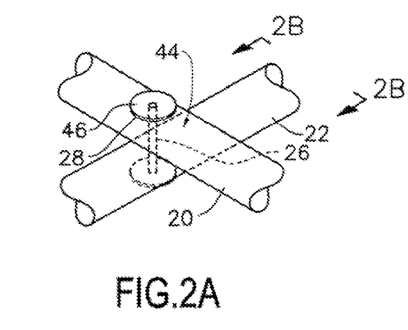
FIG. 2A shows a side view of an embodiment of a braid intersection.
Figure 2B:
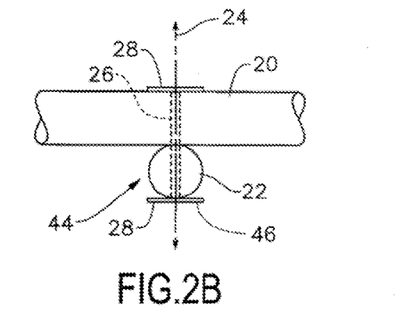
FIG. 2B shows a cross-sectional view of the braid intersection of FIG. 2A.

Turning to FIGS. 2A and 2B, in some embodiments, one or more of the braid intersections 44 has a rivet 46 extending therethrough. The braid intersections 44 are formed at the overlap of a first wire segment 20 and a second wire segment 22. The first and second wire segments 20, 22 are able to pivot or scissor about rivet axis 24.

In some embodiments, the rivet 46 comprises a central portion 26 and end portions 28 on either side of the central portion 26. The end portions 28 have a greater cross-sectional area than the central portion 26. In some embodiments, the rivet 46

In some embodiments, the rivet 46 is inserted through holes in the first and second wire segments 20, 22. In some embodiments, the holes are cut through the wire segments 20, 22 by way of Electrical Discharge Machining (EDM) or laser cutting. Other methods are also suitable.

In some embodiments, the rivet 46 is a blind rivet. In some embodiments, the rivet 46 is a solid rivet. In some embodiments, the rivet 46 pins the braid intersection 44 together without a tight interference fit between the central portion 26 and the hole through which it extends. In this way, the first and second wire segments 20, 22 are permitted to freely scissor about the rivet axis 24 without deformation.

In some embodiments, the rivet 46 is made from the same material as the wire segments 20, 22 to prevent corrosion due to dissimilar materials. In particular, in some embodiments, the rivets 46 are made from titanium or a nickel-titanium alloy. Other materials are also suitable.

As shown in FIGS. 3A-D, in some embodiments, the anchor 42 is formed in a plurality of rows 30 and a plurality of columns 32. The rows 30 and columns 32 intersect one another at the braid intersections 44. For the purpose of illustration, the rows 30 are labeled A through O' and columns are labeled 1 through 15.5, as shown.

Figure 3A:
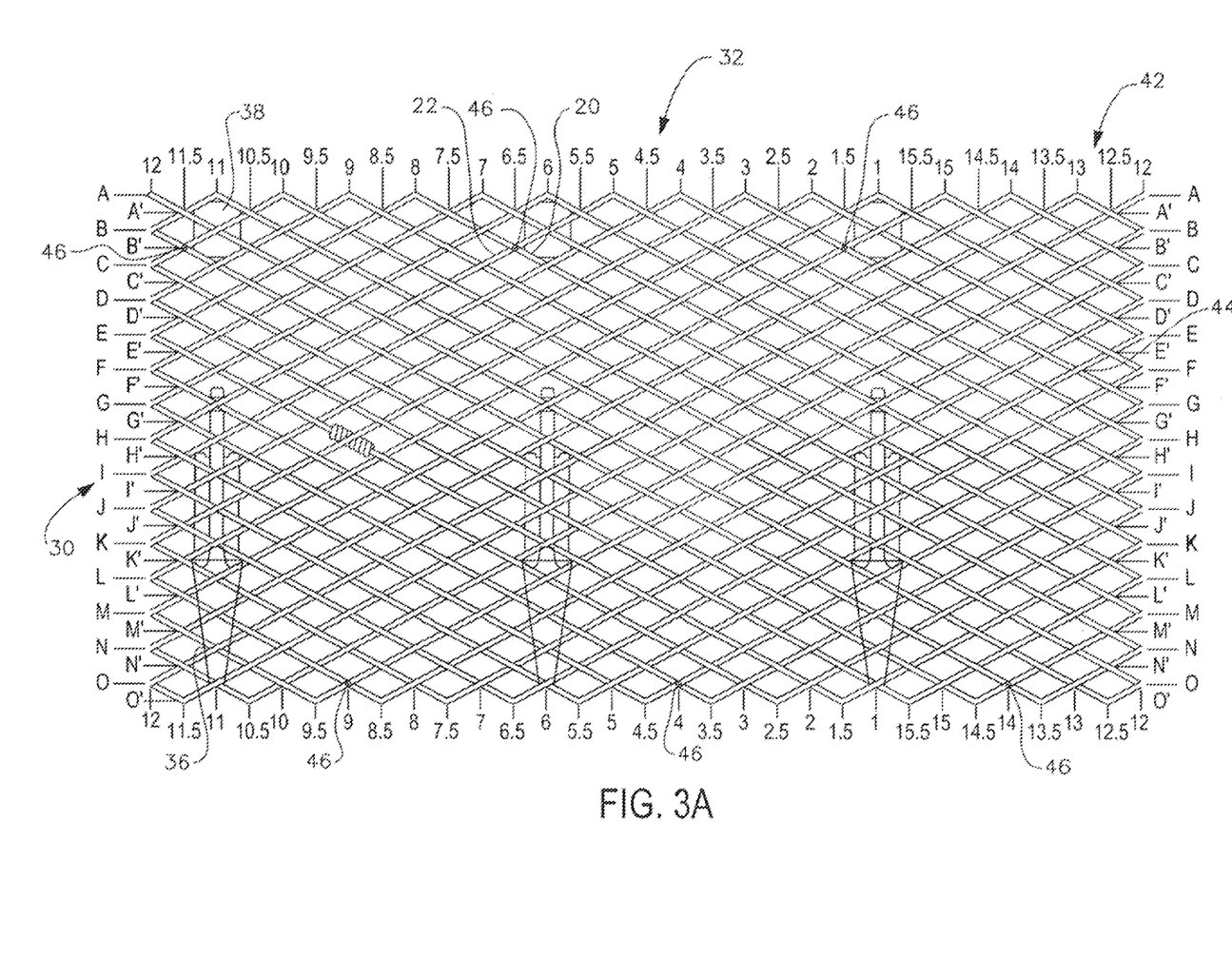
FIGS. 3A-3D show flat-patterns of the braid anchor 42.

In some embodiments, the anchor 42 has a plurality of posts 36 and buckles 38. In some embodiments, the posts 36 engage the buckles 38 as discussed in US Publication No. 2005/0143809, which is herein incorporated by reference. As shown in FIG. 3A, in some embodiments, the anchor 42 has rivets 46 adjacent to buckles 38 and in between posts 36. In particular, as shown, each buckle 38 has a single rivet 46 at an adjacent braid intersection 44. Rivets 46 are placed along row B' at columns 11.5, 6.5, and 1.5.

As further shown in FIG. 3A, rivets 46 are disposed along row O at columns 9, 4, and 14, staggered between posts 36. Row O is the first row from the bottom 48 or inlet side of the anchor 42. In some embodiments, rivets 46 are placed between posts 36 and near the bottom 48 of anchor 42 in order to provide fatigue resistance. In particular, in some embodiments, stress is induced in the anchor 42 due to actuation of the replacement heart valve 40 (FIG. 1) as it operates. Without being bound by a particular theory, it is believed that placement of the rivets 46 between posts 36 reduces fatigue in the anchor 42. Moreover, in some embodiments, the rivets 46 prevent overlapping first and second wire segments 20, 22 from being pulled apart as the replacement heart valve 40 actuates. In some embodiments, rivets 46 prevent first and second wire segments 20, 22 from being pulled apart in a radial direction, an axial direction, and a circumferential direction. Nonetheless, the first and second wire segments 20, 22 can pivot relative to another about rivet axis 24 (FIG. 2B).

Figure 3B:
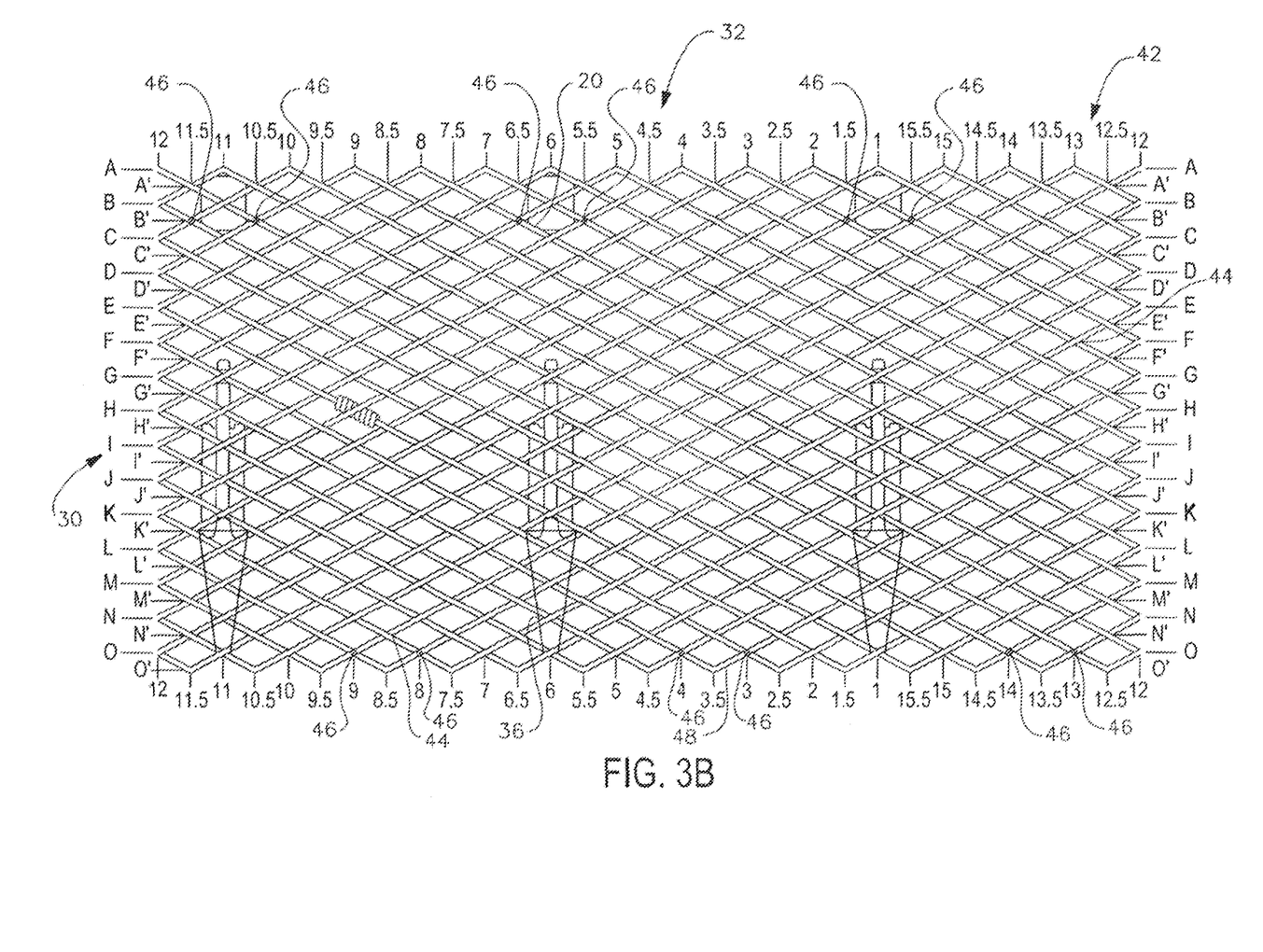

Turning to FIG. 3B, in some embodiments, rivets 46 are placed on both sides of the buckles 38, for example along row B' at columns 11.5, 10.5, 6.5, 5.5, 1.5, and 15.5. Further, rivets 46 are placed between posts 36 along row O at columns 9, 8, 4, 3, 14, and 13. In this way, there are two adjacent braid intersections 44 along row O with rivets 46, followed by a braid intersection 44 without a rivet, followed by a post 36, followed by another braid intersection 44 without a rivet, followed by two rivets 46 at adjacent braid intersections 44.

Figure 3C:
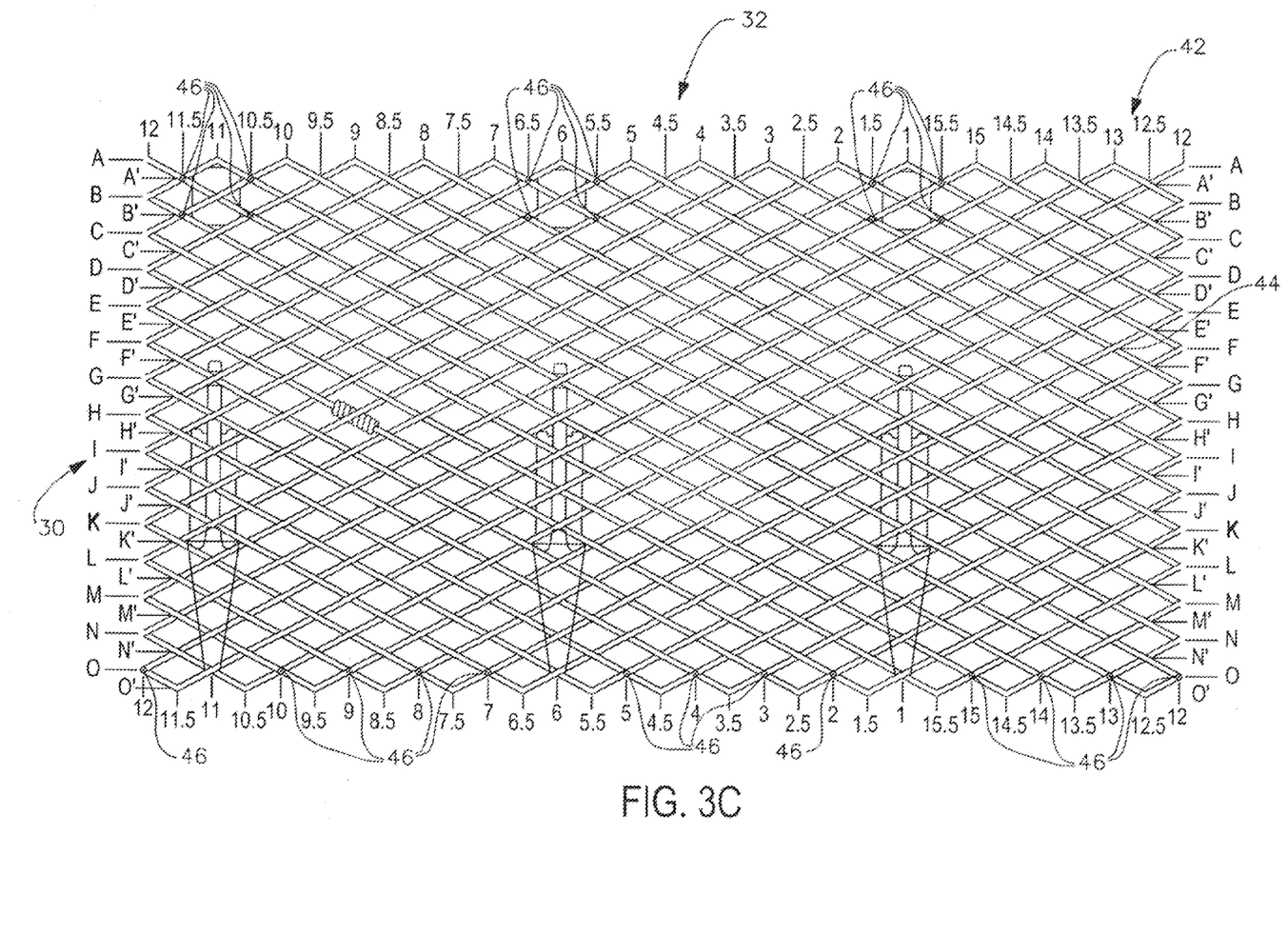

As shown in FIG. 3C, the anchor 42 comprises two rivets 46 on either side of the buckles 38. In some embodiments, rivets 46 are located along row A' at columns 11.5, 10.5, 6.5, 5.5, 1.5, and 15.5 and along row B' at columns 11.5, 10.5, 6.5, 5.5, 1.5, and 15.5. In addition, rivets 46 are located along row O at columns 10, 9, 8, 7, 5, 4, 3, 2, 15, 14, 13, and 12.

Figure 3D:
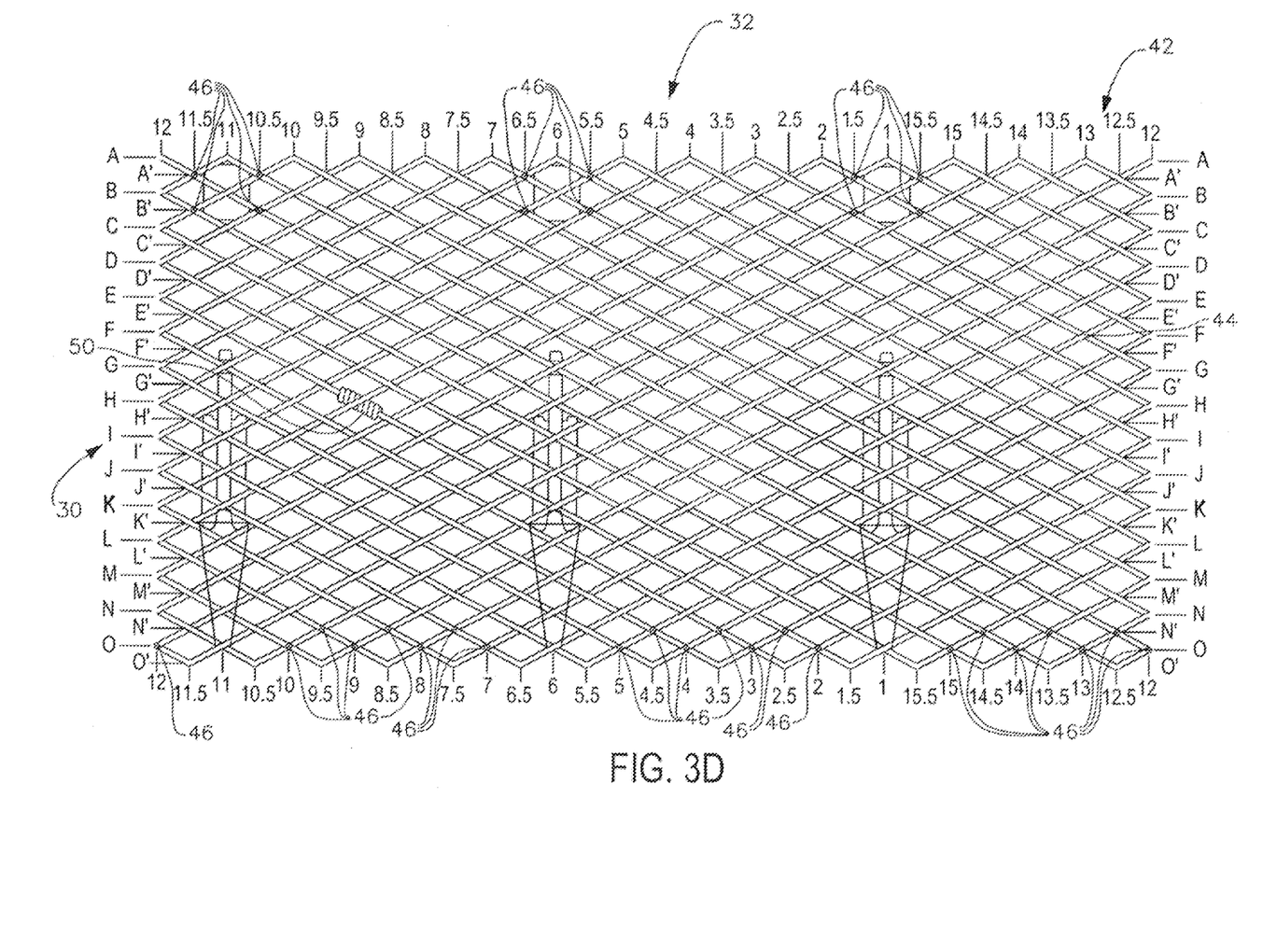

With reference to FIG. 3D, the anchor 42 comprises two rivets 46 on either side of the buckles 38. In some embodiments, rivets 46 are located along row A' at columns 11.5, 10.5, 6.5, 5.5, 1.5, and 15.5 and along row B' at columns 11.5, 10.5, 6.5, 5.5, 1.5, and 15.5. Additionally, in some embodiments, rivets 46 are located along row N' at columns 9.5, 8.5, 7.5, 4.5, 3.5, 2.5, 14.5, 13.5, and 12.5 and along row O at columns 10, 9, 8, 7, 5, 4, 3, 2, 15, 14, 13, and 12.

As further shown in each of FIGS. 3A-3D, in some embodiments, the anchor 46 has a radiopaque marker 50. The radiopaque marker 50 provides visibility during and after implantation of the anchor 42. In some embodiments, the radiopaque marker 50 is made from tantalum. Other radiopaque materials can also be used.

Figure 4:
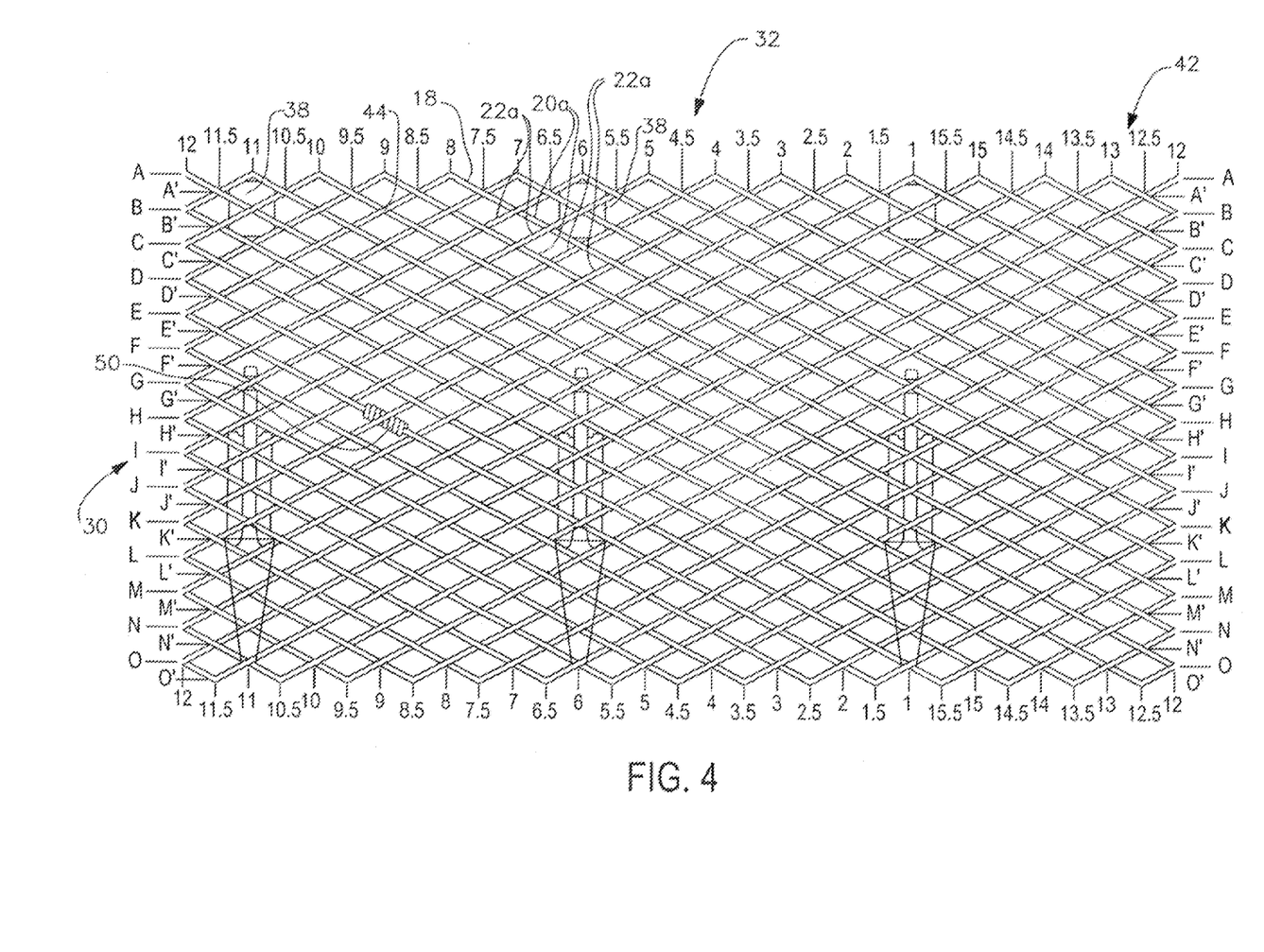
FIG. 4 shows a flat-pattern of an embodiment of the braid anchor 42.

Turning to FIG. 4, an anchor 42 is shown therein having a woven braid structure comprising a plurality of braid intersections 44. Throughout most of the woven braid structure of the anchor 42, the wire 18 follows an over-under-over-under pattern of weaving. In this way, the wire 18 is woven over an intersecting segment of wire and woven under the adjacent intersecting segment, and so-forth. Along portions of the anchor 42, for example at or near the buckles 38, however, the wire 18 is woven in a modified pattern. As shown for example at column 7, row C; column 6.5, row B; and column 6, row B, the second wire segment 22a is routed over three adjacent first wire segments 20a. Further, at column 7, row B and column 6.5, row B', the second wire segment 22a is routed over the adjacent first wire segments 20a. Finally, at column 6, row C and column 5.5, row C', the first wire segment 20a is routed over the adjacent second wire segments 22a.

In some embodiments, the anchor 42 follows this modified pattern at the braid intersections 44 adjacent to the buckles 38. In some embodiments, this modified pattern reduces wear in the wire 18. Without being bound by a particular theory, it is believed that due to loading and separation of first and second wire segments 20a, 22a at the braid intersections 44 near the buckles 38, the wire 18 of the wire segments 20a, 22a near the buckles 38 undergoes more wear than at braid intersections 44 that are further away from the buckles 38. The loading and separation is caused by actuation of the replacement heart valve 40 (FIG. 1). In particular, as the replacement heart valve 40 actuates, it flexes the first and second wire segments 20a, 22a. Moreover, the wire segments 20a, 22a near the buckles 38 experience the greatest amount of stress because, in some embodiments, the replacement heart valve 40 is attached to the buckles 38 which are, in turn, attached to the wire segments 20a, 22a of the anchor 42. Consequently, actuation of the replacement heart valve 40 separates the first and second wire segments 20a, 22a at the braid intersections 44 by pulling them apart in a radial direction (in/out of the page in the flat pattern of FIG. 4). In some embodiments, for example as shown in FIG. 4, arranging the wire 18 in such a modified pattern at the braid intersections 44 adjacent to the buckles 38, decreases wire wear. In addition to the foregoing, in some embodiments, the wire 18 is routed in such a modified pattern at the braid intersections 44 adjacent to each of the buckles 38.

In some embodiments, the anchor 42 has a different braid density at the bottom 48 of the anchor 42 than at the top 64 or outlet. In some embodiments, the braid wires 18 are closer together at the bottom 48 of the anchor 42 than at the top 64. In some embodiments, the bottom 48 or inlet side of the anchor 42 experiences greater loading due to opening and closing of the replacement heart valve 40 than does the top 64 of the anchor 42. Consequently, in some embodiments, the area(s) of greater loading have a higher braid density, with more braid intersections 44 per unit area, than the area(s) of lesser loading.

In some embodiments, a higher braid density is achieved by varying the pin spacing on the braid mandrel. An example of a braid mandrel is shown in FIGS. 3-4D of US Publication No. 2008/0125859, which is herein incorporated by reference. Moreover, in some embodiments, the wire is heat-set on the mandrel to maintain the shape of the anchor 42 upon removal from the mandrel.

Figure 7:
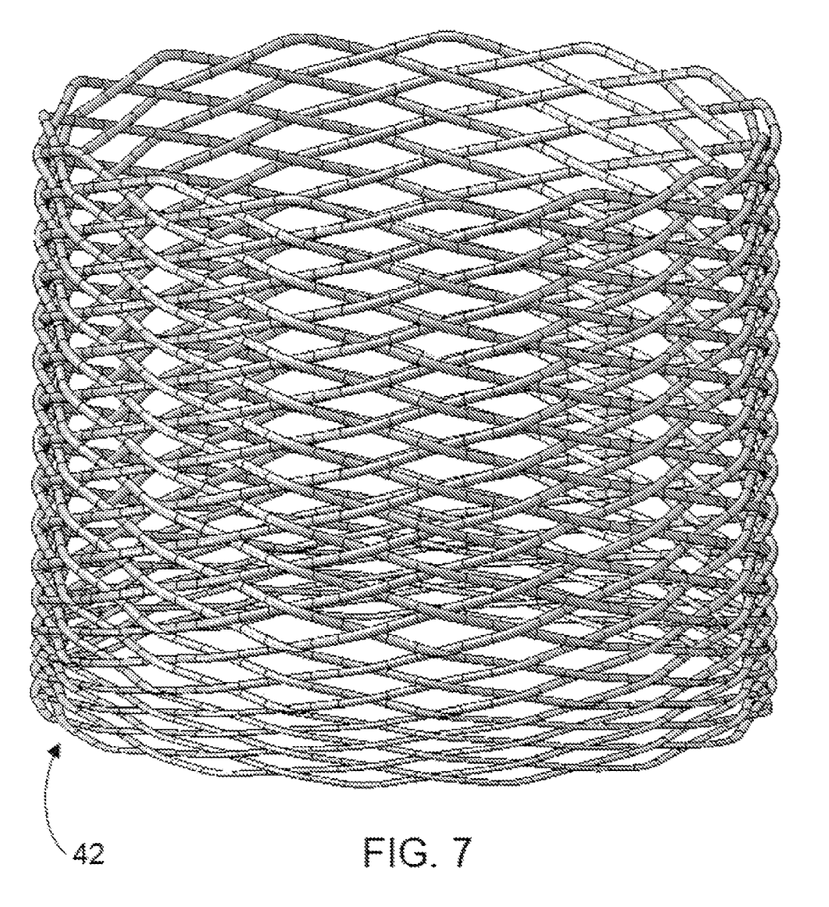
FIGS. 7 and 8 show embodiments of the braid anchor 42 having a variable braid density.
Figure 8:
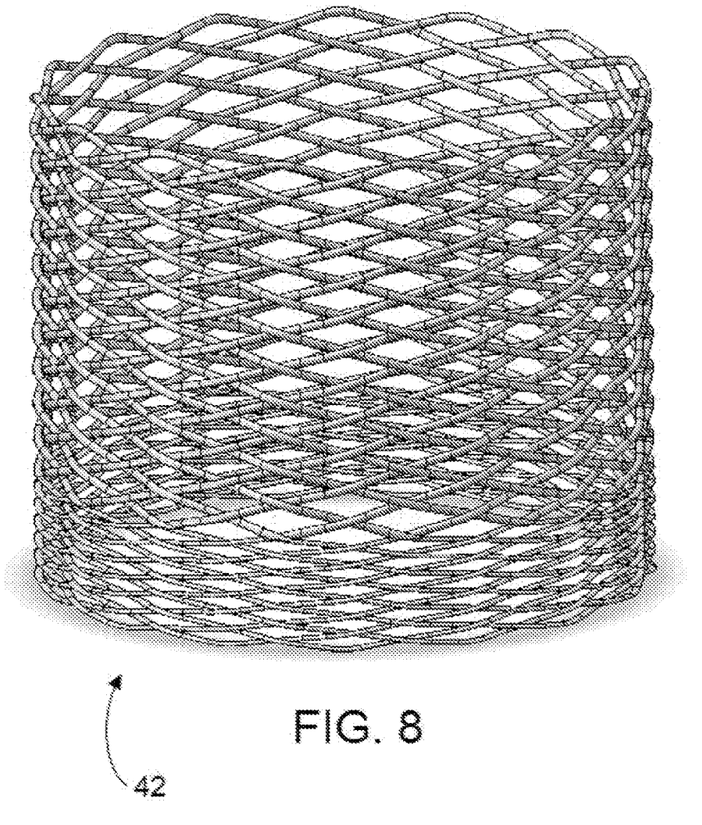

Further, in some embodiments, the braid density increases gradually throughout the length of the anchor 42. In some embodiments, however, the change in braid density is more abrupt. Suitable embodiments of anchors 42 having increased braid density along a portion of the anchor are shown for example in FIGS. 7 and 8.

In some embodiments, the wire 18 is formed from a nickel-titanium alloy. Additionally, in some embodiments, the wire 18 is heat treated and a wear resistant oxide layer is formed on the surface of the wire 18. In some embodiments, the entire length of the wire 18 has an oxide layer. Alternatively, in some embodiments, only portions of the wire 18 have an oxide layer.

Figure 5:
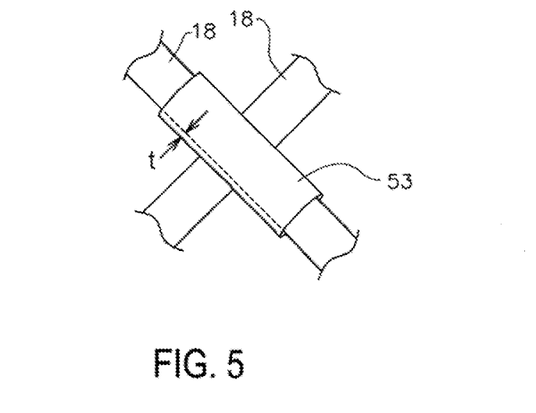
FIG. 5 shows an embodiment of a braid intersection having a coating thereon.

Turning to FIG. 5, in some embodiments, the wire 18 has a biocompatible coating 53 over a portion, or the entire length, thereof. Further, in some embodiments, the biocompatible coating 53 promotes tissue growth at the braid intersections 44. In some embodiments, the biocompatible coating 53 comprises polyurethane. Moreover, in some embodiments, the biocompatible coating 53 is placed on the wire 18 at the braid intersections 44 and the portions of wire 18 between the braid intersections 44 do not have biocompatible coating thereon. In some embodiments, portions of the wire 18 are masked off prior to coating. In this way, the wire 18 can have biocompatible coating 53 on selected portions. Having biocompatible coating 53 on only selected portions of the wire 18 can be advantageous when compared to embodiments having the coating over the entire length of the wire 18. In particular, the biocompatible coating 53 has a thickness, t, which can increase the profile of the anchor 42 in its unexpanded configuration. Coating only selected portions of the wire 18 with the biocompatible coating 53, however, permits the anchor 42 to have a smaller profile in the unexpanded configuration, thereby reducing the potential for complications during the implantation procedure.

In some embodiments, the wire 18, or portions thereof, is pre-strained in tension. This provides the anchor 42 with improved fatigue life. In particular, opening and closing of the replacement heart valve 40 applies a cyclical load to the braid wires 18, especially where the braid wires 18 are attached to the replacement heart valve 40. The loading induces strain in the braid wires 18, which causes fatigue.

Figure 6A:
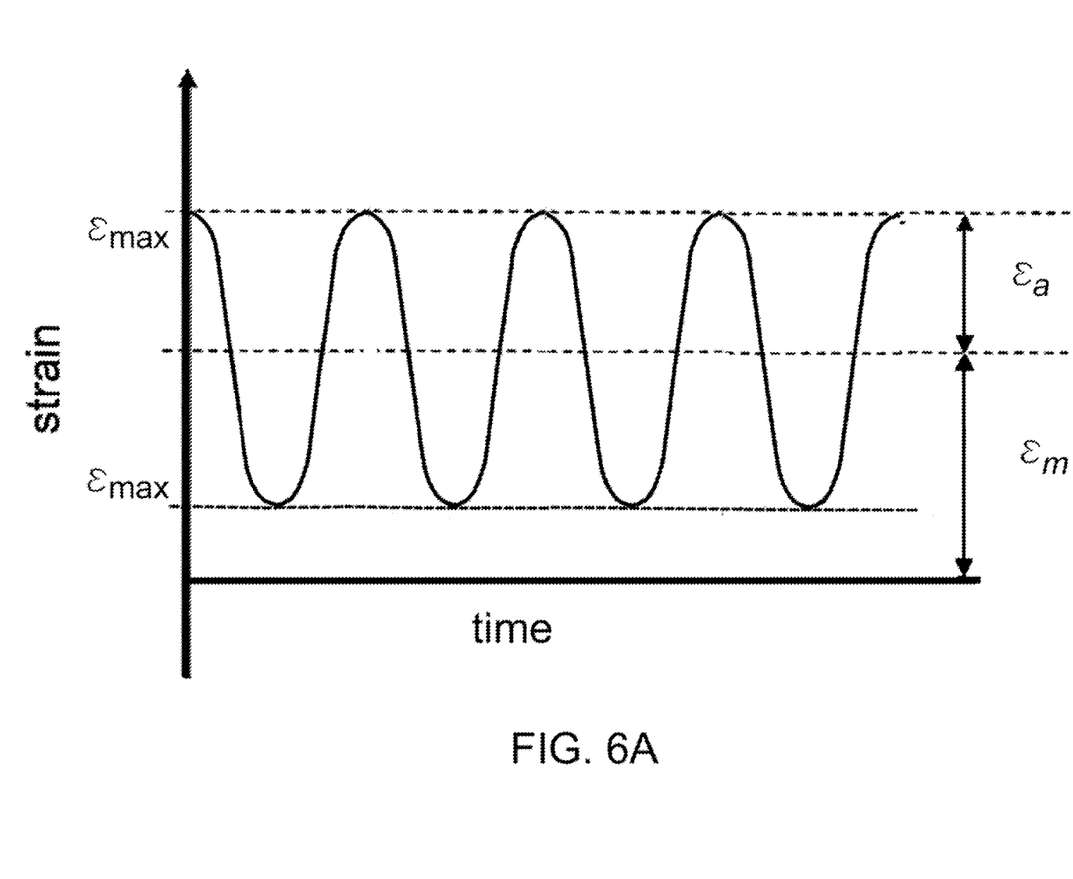
FIG. 6A shows a strain plot.

The strain can be broken down into two components, namely "mean strain," $\varepsilon_m$ and "alternating strain," $\varepsilon_a$. As will be appreciated by the skilled artisan, in a reversing load application, the alternating strain, $\varepsilon_a$, is defined as ½ of the peak-to-peak strain, or:

$$\varepsilon_a = \frac{\varepsilon_{max} - \varepsilon_{min}}{2} \quad \text{\#\#EQU00001\#\#}$$

where $\varepsilon_{max}$ is the maximum strain and $\varepsilon_{min}$ is the minimum strain, for example as shown in FIG. 6A. Further, the mean strain, $\varepsilon_m$, is defined as:

$$\varepsilon_m = \frac{\varepsilon_{max} + \varepsilon_{min}}{2} \quad \text{\#\#EQU00002\#\#}$$

Figure 6B:
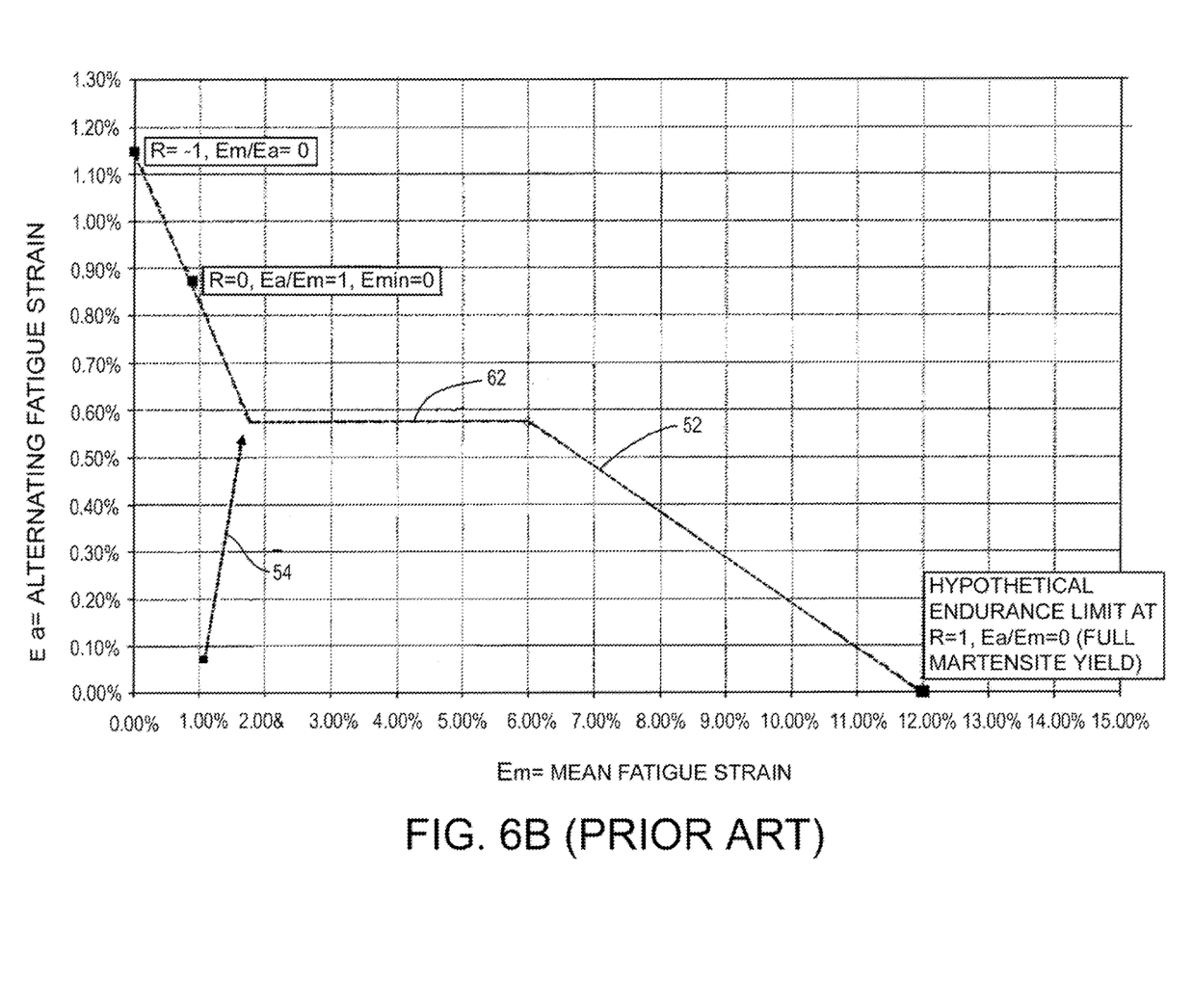
FIG. 6B shows a PRIOR ART Goodman Diagram.
Figure 6C:
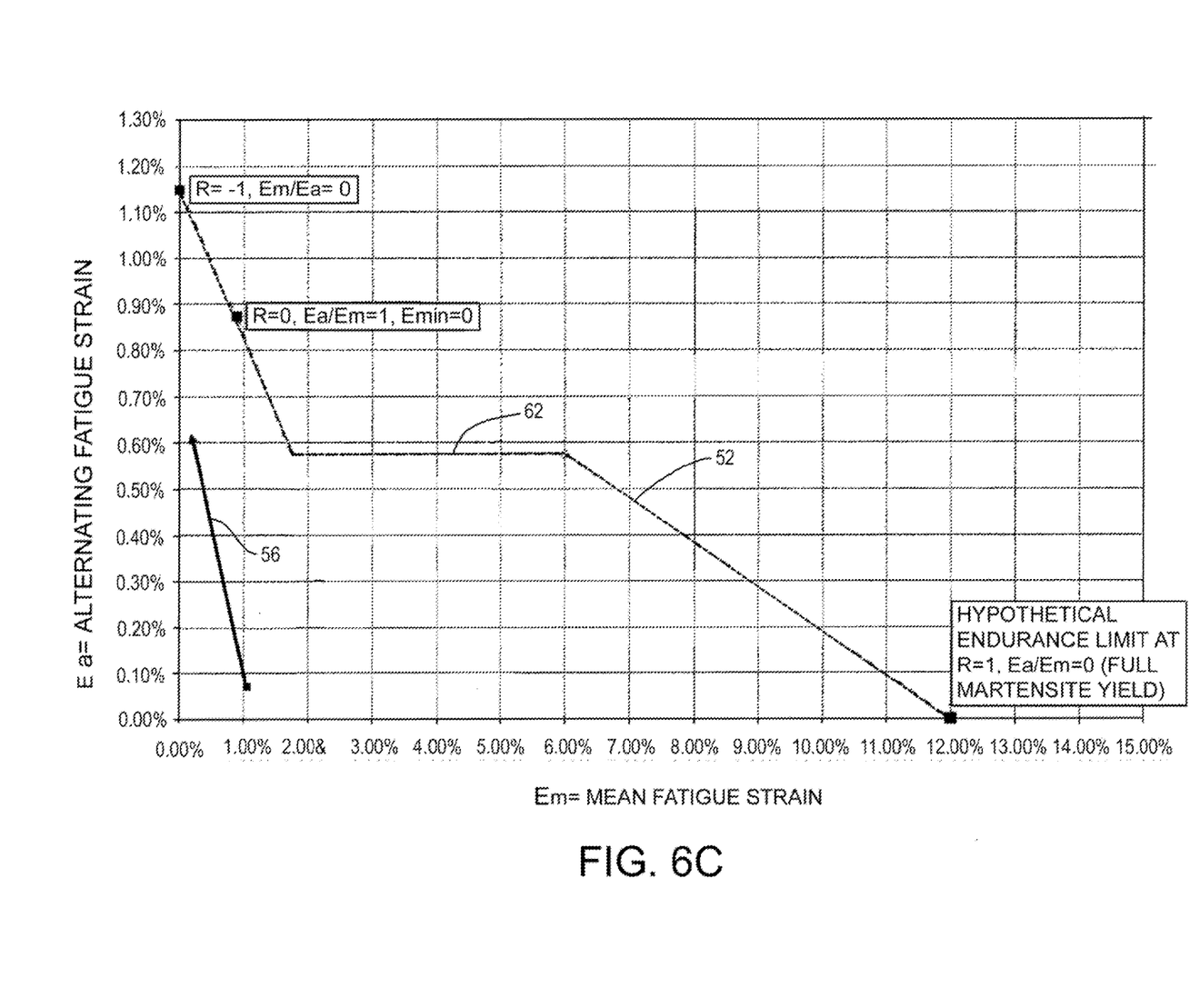
FIG. 6C shows a Goodman Diagram of an embodiment of the braid anchor 42.

Turning to FIGS. 6B and 6C, strain-based Goodman Diagrams are shown therein depicting a typical Nitinol fatigue failure envelope at reference numeral 52. Further shown along the limits of the fatigue failure envelope 52 are the values of R, the strain ratio in fatigue cycling. In general:

$$R = \varepsilon_{min} / \varepsilon_{max} \quad \text{\#\#EQU00003\#\#}$$

Additionally, R is equal to negative one where the mean strain, $\varepsilon_m$, is zero and the alternating strain, $\varepsilon_a$, is fully reversing. R is equal to zero wherein the mean strain, $\varepsilon_m$, and the alternating strain, $\varepsilon_a$, are equal; $\varepsilon_{min}$ is zero in this instance. Finally R is equal to positive one when the alternating strain, $\varepsilon_a$, is equal to zero.

FIG. 6B depicts the strain relationship of a PRIOR ART replacement valve stent, shown with dashed line 54. In particular, a PRIOR ART self-expanding valve stent expands to a diameter equal to or smaller than its stress free diameter. When such a valve stent is implanted and operating, the valve portion opens and closes to permit proper blood flow. When the valve portion is open, the strain on the self-expanding stent is at a minimum. In this case, the strain is at a constant, k, greater than or equal to zero, as shown below:

$$\varepsilon_{min} = k \geq 0$$

Moreover, when the valve portion of the PRIOR ART self-expanding valve stent is in a closed configuration, the strain increases to a maximum strain $\varepsilon_{max}$. The PRIOR ART self-expanding valve stent can therefore be modeled as:

$$\varepsilon_{min} = \varepsilon_m - \varepsilon_a = k \geq 0$$

This, in-turn, can be re-written as:

$$\varepsilon_m = \varepsilon_a + k$$

It will appreciated, therefore, that the slope of the line modeling the PRIOR ART self-expanding valve stent is one (1), as shown in FIG. 6B with reference numeral 54. It will further be appreciated that with increasing mean strain, $\varepsilon_m$, the average strain, $\varepsilon_a$, also increases.

Contrastingly, and turning to FIG. 6C, in some embodiments, the braided wires 18 of the immediate replacement heart valve anchor 42 (FIG. 1) are pre-strained to counteract physiological loading. In particular, in some embodiments, upon implantation, the anchor 42 is expanded to a diameter larger than its stress free diameter. In this instance, the braid wires 18 are in tension when the anchor 42 is expanded, and without any applied loading from the replacement heart valve 40. During operation, the replacement heart valve 40 applies additional force to the anchor 42. Specifically, in some embodiments, for example as shown in FIG. 1, the replacement heart valve 40 is attached to the anchor 42, in-part, along the bottom 44. As a result, when the replacement heart valve 40 opens and closes it induces strain on the anchor 42. In some embodiments, the strain is concentrated along the bottom 44 in regions opposite the apex 58 of the valve leaflet 60.

In some embodiments of the immediate anchor 42, maximum tension in the braid wires 18 occurs when the replacement heart valve 40 is open. In this way, the strain is at a maximum, $\varepsilon_{max}$. Additionally, in some embodiments, the strain is reduced as the replacement heart valve 40 closes, reaching a minimum, $\varepsilon_{min}$, when the replacement heart valve 40 is closed. As described previously, it will be appreciated that in some embodiments this occurs because the anchor 42 has been expanded to a diameter larger than its stress free diameter. Consequently, the maximum strain, $\varepsilon_{max}$, is equal to the sum of the mean strain, $\varepsilon_m$, and the alternating strain, $\varepsilon_a$. In algebraic form, the anchor 42 can be modeled as:

$$\varepsilon_{max} = \varepsilon_m + \varepsilon_a$$

This, in turn, can be re-written as:

$$\varepsilon_m = \varepsilon_{max} - \varepsilon_{alpha}$$

where $\varepsilon_{max}$ is the strain induced upon expansion and implantation of the anchor 42, and can be set to a predetermined value.

It will appreciated, therefore, that the slope of the line modeling the immediate anchor 42 stent is negative one (−1), as shown in FIG. 6C with reference numeral 56. It will further be appreciated that with increasing mean strain, .epsilon..sub.m, the average strain, .epsilon..sub.a, decreases. As further shown in FIG. 6C, the behavior of the immediate anchor, modeled via line 56, is expected to have a greater fatigue life than the known PRIOR ART self-expanding valve stents, as modeled via line 54 in FIG. 6B, because line 56 extends away from the horizontal fatigue failure limit line 62.

In addition to the foregoing, and without being bound by a particular theory, it is believed that line 56 is more likely to remain in the austenitic phase of the nickel-titanium alloy, for example Nitinol®, than that of line 54, thereby further reducing the likelihood of material fracturing due to phase change.

In some embodiments, the curvature of the wire 18 is increased at the braid intersections 44 and reduced between braid intersections 44. In this way, in some embodiments, at the braid intersections 44, the wires 18 are curved to maximize contact therebetween. Without being bound by a particular theory, this is believed to reduce localized wear in the wire 18 at the intersections 44 by increasing the contact patch between the wires 18 at the braid intersections 44. Additionally, in some embodiments, the wire 18 cross-section is flattened at the braid intersections 44. Further, in some embodiments, one or more of the intersecting wires 18 is notched at the braid intersections 44. In some embodiments, the wire 18 is has a reduced or increased cross-section at the braid intersections 44. Finally, in some embodiments, the wire 18 has a non-uniform cross-section; for example, in some embodiments, portions of the wire have circular cross-sections while other portions have oval cross-sections. Other suitable geometries can also be employed.

Further, in some embodiments, the wire 18 undergoes an electro-polishing process. In some embodiments, the electro-polishing process is a multi-stage process wherein the wire diameter of the wire 18 is reduced by 20%. In some embodiments, the multi-stage process involves electro-polishing the entire length of the wire in a first step. Subsequently, only portions of the wire 18 are polished to selectively reduce the diameter of the wire 18 in specific locations. For example, in some embodiments, the portion of the wire 18 forming the top 64 of the anchor 42 are only polished a single time, while the remainder of the wire 18 is polished two or more times.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

What is claimed is:

1. An apparatus for replacing a native heart valve comprising:
   an expandable anchor having a central longitudinal axis;
   a replacement heart valve attached to the expandable anchor; and
   a plurality of rivets;
   the expandable anchor comprising a woven braid structure surrounding at least a portion of the replacement heart valve, the woven braid structure having a plurality of braid intersections, each braid intersection having a first wire segment and a second wire segment overlapping the first wire segment,
   wherein the woven braid structure defines an inflow end and an outflow end;
   each of the plurality of rivets extending through the first wire segment and the second wire segment at one of the plurality of braid intersections along a radial axis normal to the central longitudinal axis,
   wherein at least some of the plurality of braid intersections of the woven braid structure between the inflow end and the outflow end of the woven braid structure are free of the plurality of rivets;
   wherein the first wire segment is hingeable with respect to the second wire segment along the radial axis,
   a plurality of buckles attached to the expandable anchor; and
   a plurality of posts insertable into the plurality of buckles;
      wherein the plurality of rivets is disposed between the plurality of posts at consecutive braid intersections along the inflow end of the woven braid structure.

2. The apparatus of claim 1,
   wherein one rivet of the plurality of rivets is disposed at an immediately adjacent braid intersection on each side of each of the plurality of buckles.

3. The apparatus of claim 2, wherein two of the plurality of rivets are disposed at immediately adjacent braid intersections on each side of each of the plurality of buckles.

4. The apparatus of claim 1, wherein the expandable anchor has a variable braid density along a length of the woven braid structure.

5. The apparatus of claim 4, wherein the braid density increases gradually throughout the length of the woven braid structure.

6. The apparatus of claim 5, wherein the inflow end of the woven braid structure has a greater braid density than the outflow end of the woven braid structure.

7. The apparatus of claim 1, wherein the expandable anchor is expandable from an unexpanded configuration to an expanded configuration.

8. The apparatus of claim 7, wherein in the expanded configuration, the expandable anchor is expanded to a diameter greater than a stress-free diameter in the unexpanded configuration.

9. The apparatus of claim 7, wherein in the expanded configuration, the first wire segments and the second wire segments of the woven braid structure are in tension.

10. An apparatus for replacing a native heart valve comprising:
- an expandable anchor having a central longitudinal axis;
- a replacement heart valve attached to the expandable anchor; and
- a plurality of rivets;
- the expandable anchor comprising a woven braid structure surrounding at least a portion of the replacement heart valve, the woven braid structure having a plurality of braid intersections, each braid intersection having a first wire segment and a second wire segment overlapping the first wire segment, wherein the woven braid structure defines an inflow end and an outflow end;
- each of the plurality of rivets extending radially outward through the first wire segment and the second wire segment at one of the plurality of braid intersections,
- wherein at least some of the plurality of braid intersections of the woven braid structure between the inflow end and the outflow end of the woven braid structure are free of the plurality of rivets,
- wherein the first wire segment is hingeable with respect to the second wire segment about the rivet extending therethrough;
- wherein a biocompatible coating is disposed on the woven braid structure at the plurality of braid intersections, wherein portions of the woven braid structure between the braid intersections do not have the biocompatible coating thereon,
- a plurality of buckles attached to the expandable anchor; and
- a plurality of posts insertable into the plurality of buckles;
- wherein the plurality of rivets is disposed between the plurality of posts at consecutive braid intersections along the inflow end of the woven braid structure.

11. The apparatus of claim 10,
wherein one rivet of the plurality of rivets is disposed at an immediately adjacent braid intersection on each side of each of the plurality of buckles.

12. The apparatus of claim 10, wherein the expandable anchor is configured to shift between a collapsed configuration and an expanded configuration.

13. The apparatus of claim 12, wherein the expandable anchor is configured to reversibly shift between the collapsed configuration and a partially-expanded configuration.

14. The apparatus of claim 10, wherein the woven braid structure includes a wear resistant oxide layer formed thereon.

15. The apparatus of claim 10, wherein the biocompatible coating comprises polyurethane.

16. The apparatus of claim 10, wherein the expandable anchor is expandable radially from an unexpanded configuration to an expanded configuration.

17. The apparatus of claim 16, wherein in the expanded configuration, the first wire segments and the second wire segments of the woven braid structure are in tension.

* * * * *